United States Patent [19]

Mercer et al.

[11] Patent Number: 4,520,802

[45] Date of Patent: Jun. 4, 1985

[54] BI-AXIAL ORTHOTIC DEVICE

[76] Inventors: James D. Mercer, 100 Silverwood Dr., Lafayette, Calif. 94549; Gordon Aaserude, 444 La Palomba, El Sobrante, Calif. 94803

[21] Appl. No.: 537,795

[22] Filed: Sep. 30, 1983

[51] Int. Cl.³ ............................................... A61F 3/00
[52] U.S. Cl. .................. 128/80 C; 128/80 F; 128/88; 3/26
[58] Field of Search .................. 128/80 C, 80 F, 87 R, 128/88; 3/22, 26, 27, 28

[56] References Cited

U.S. PATENT DOCUMENTS 2,812,760 11/1957 Miller .............................. 128/80 F
3,030,634 4/1962 Bair .................................. 128/88 X
3,187,347 6/1965 Terron ...................................... 3/26

Primary Examiner—John D. Yasko
Attorney, Agent, or Firm—Harry A. Pacini

[57] ABSTRACT

An improved bi-axial hinged orthotic device for use in knee braces, stabilizers, modified cast and fracture braces that allows movement of the leg and knee, providing lateral support, protection and rotational stability of a knee-joint and ligaments consisting essentially of a three-segment double hinged single side brace employed in a paired configuration; said brace having a rigid support bar or rod positioned opposite the knee-joint; index blocks positioned on the support bar coact with one end of the upper flex bar and at the other end with a lower flex bar; the upper flex bar secured to a first attachment anchor and the lower flange secured to a second attachment anchor; each attachment anchor can be used for securely embedding in casting material one end over the thigh and one end over the lower leg or calf; said double hinged brace modified with index blocks for limiting flexion and extension of the knee joint and leg.

5 Claims, 12 Drawing Figures

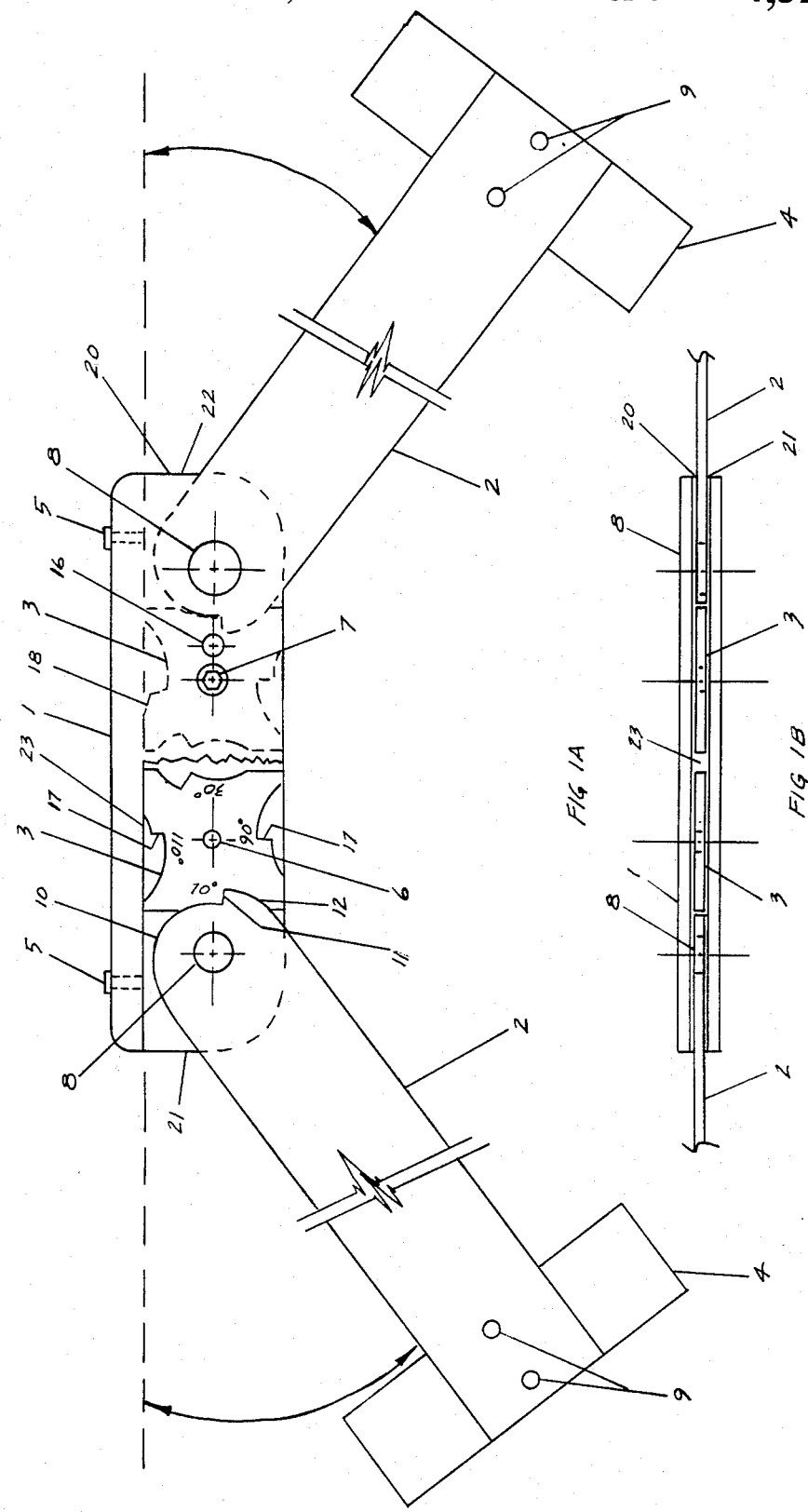

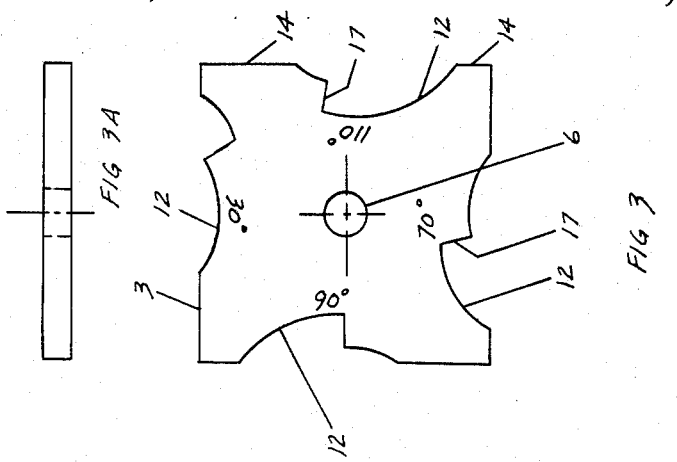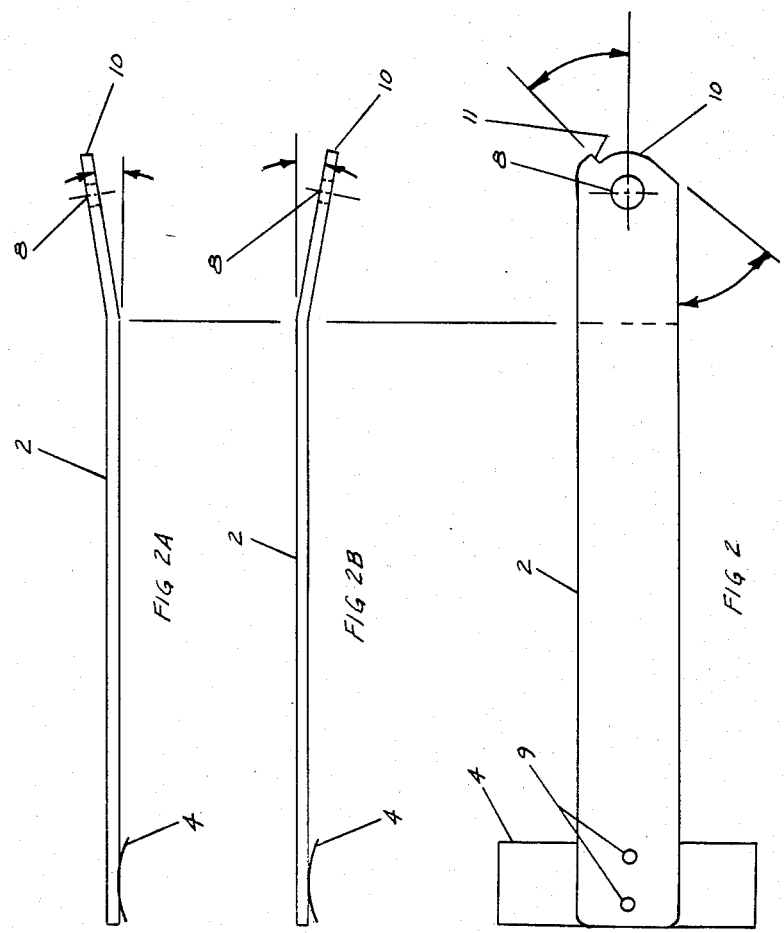

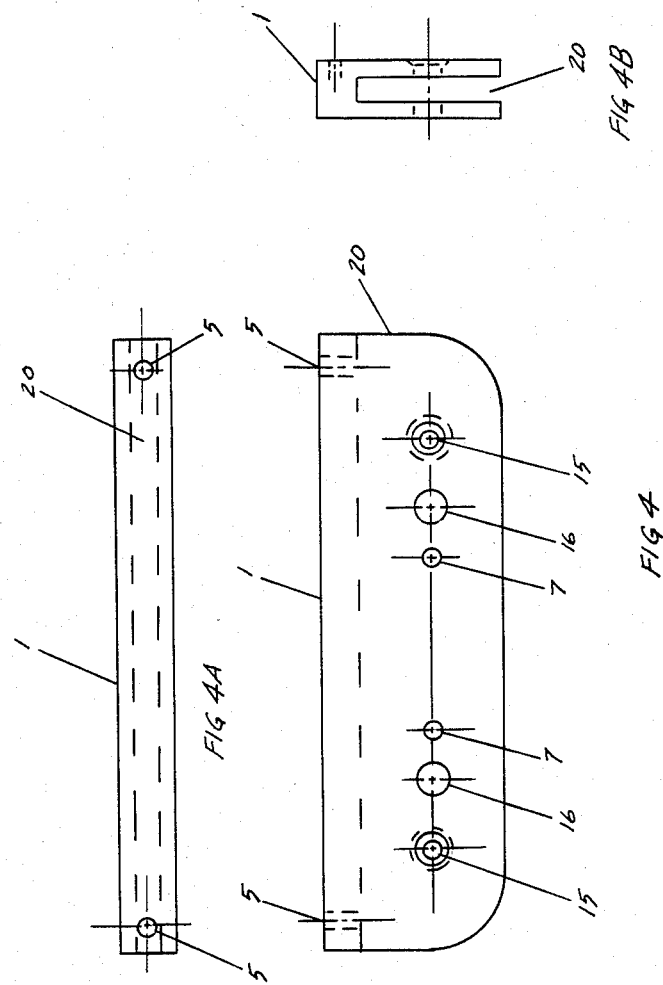

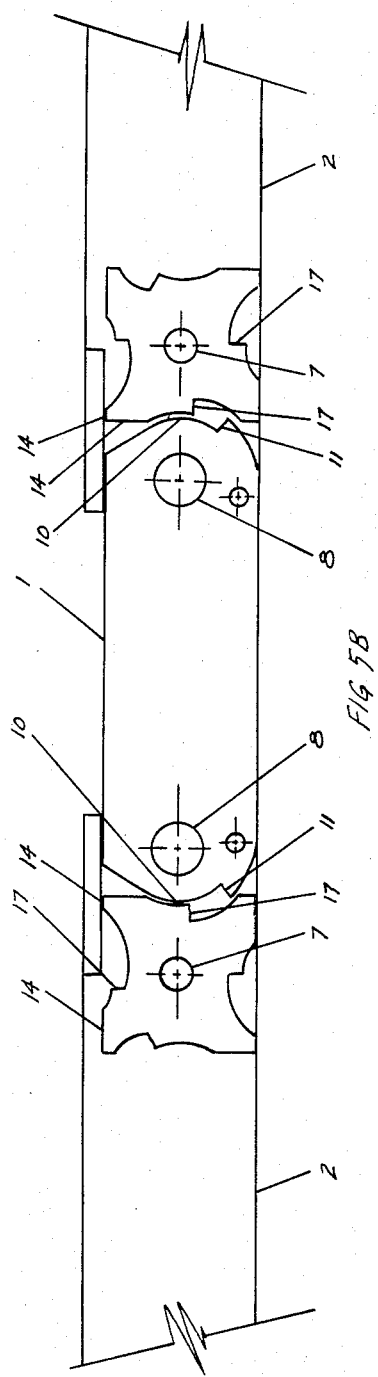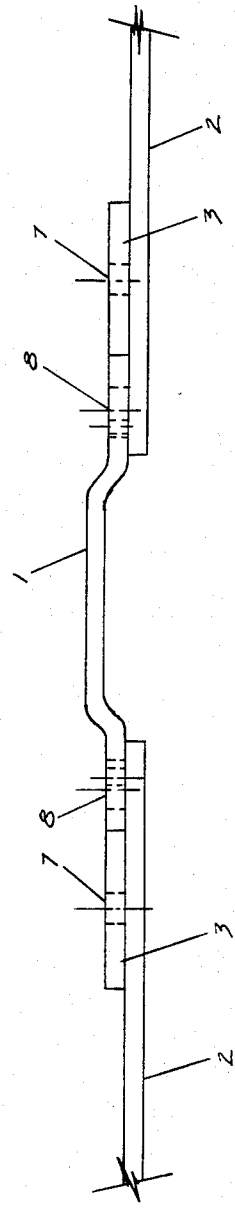

BI-AXIAL ORTHOTIC DEVICE

BACKGROUND OF THE INVENTION

This invention relates to an improved orthotic device for use in a new assembly of knee brace or knee stabilizer and modified cast brace. More particularly, this invention relates to a new and improved bi-axial hinged side brace orthotic device with flexion and extension limiter inserts, such as index blocks, for use in support and alignment of the knee joints, security of limb position, prevention of change in position attributed to rotatory forces on the fracture site, prevention of injury or reinjury, prevention of swelling complications, and economy of physician's time. Support and protection is useful for medial or lateral application.

The knee-joint is made up of two condyloid joints and a third joint, partly arthrodial, but not completely so, since the articular surfaces are not mutually adapted to each other, so that the movement is not a simple gliding one. The principle movements that take place at the knee-joint are flexion and extension. The movement of flexion and extension at this joint differ from those in a typical hinge joint, such as the elbow, in that the axis around shich motion takes place is not a fixed one but shifts forward during extension, as a gliding movement is superimposed on the rolling, and shifts backward during flexion.

Although the knee-joint has been described as a hinge joint, it is really of a much more complicated character. It must be regarded as consisting of three articulations, of two different kinds. The first kind is a condyloid articulation; in this form of joint, an ovoid articular surface, or condyle, is received into an elliptical cavity in such a manner as to permit flexion, extension, abduction, adduction, and circumduction, but no axial rotation. The second kind of articution involved is arthrodial; this is a joint which permits only gliding movement. It is formed by the apposition of plane surfaces, or one slightly concave, the other slightly convex, the amount of motion between them being limited by the ligaments of osseous processes surrounding the articulation.

Persons who have sustained knee injuries, who have had operations to remove cartilage, or who have weak knee-joints from various causes, such as arthritis or atheletes who have sustained an injury to the medial collateral ligament or lateral collateral ligament of the knee such as hyper extension and cruciate ligaments, need protection principally against lateral motion of the knee, that is, motion may be the result, for example, of a blow to the side of the knee. At the same time, a suitable knee brace should not interfere with the normal flexion and extension of the leg. The brace should protect the knee against sidewise motions during both flexion and extension, this means that the bracing structure should continue to lie parallel to the parts of the leg above and below the knee-joint in all positions of the brace structure and should remain substantially at the knee and provide protection to the knee.

The knee-joint has four principal ligaments, one on either side and two on the inside. These ligaments may be strained or torn in sports and accidents. Injuries to these ligaments can be serious and must be properly treated if disability is to be avoided. Above all, repeated injury or strains before healing must be avoided. All degrees of ligament injuries will lead to some atrophy of the quadriceps and hamstring muscle groups.

Many previous orthotic devices for use as knee braces and protection devices have been simple hinged structures pivotable about a fixed point, which cannot move parallel to the complex motion of the knee joint. Some knee braces for support and protection of the knee-joint comprises both an inner and outer bracing structure, each a rigid planar and elongated arm and pivoted about a fixed point. The fixed point lies on and parallel to the knee and leg. During motion and a sideways blow, the rigid planar arms may cause further injury or discomfort to the already injured ligaments of the knee-joint.

Some of the previous knee braces fail to provide protection of the injured knee ligaments. While other braces may lie parallel to the leg and knee-joint while it is extended, when the leg is flexed, the bracing structure fails to follow the motion accurately.

The instant orthotic device employs a bi-axial polycentric hinge which is desirable for use with knee-joint movement, and therefore may be used in cast bracing for derotational or knee bracing; also used to distribute the load of functional below-the-knee fracture bracing. Cast bracing stresses proper alignment of the joints, security of limb position, prevention of swelling complications and economy of physician's time. A feature of this invention is the bi-axial hinged orthotic device is a brace-like device that can be utilized in paired configuration on each side of the knee-joint. The special feature of the improved modified cast brace of this invention is a modified bi-axial hinge double axis joint that restricts the arc of the leg motion to safe limits. Functionally, the use of the instant modified cast brace joint compares favorably with previous treatments. Early motion was extremely well tolerated, the stability of operated knees was well supported and aided in management of serious knee ligament injuries.

Clinical and laboratory evidence has proved that prolonged immobilization is detrimental to synovial joints. Traditional treatment of knee-joint and leg injuries commonly involves immobilization for six to eight weeks. Periods of immobilization of this length produce alterations in the biochemistry of connective tissue, the micro- and ultra-structure of synovial membrane, cartilage, tendon, and in the biomechanical properties of the ligament-bone unit. Muscle atrophy and vascular thrombi are common extra-articular complications of prolonged immobilization.

Means for minimizing the undesirable effects and management of fractures are desirable. Therefore, early protected motion will result in minimizing the undesirable effects. The instant invention is a specific modified cast brace which allows adjustable extension and flexion limits as well as locked positions of the knee motion, yet protecting healing structures from disruptive stresses.

SUMMARY OF THE INVENTION

Objects of the present invention are to provide for an improved bi-axial, orthotic device which permits and provides freedom of predetermined limited movement of the knee during flexion and extension of the leg in a cast without restriction or physical discomfort during movement.

Another object of the present invention is to provide an improved bi-axial orthotic-cast brace assembly which permits and provides freedom of optionally selected pre-determined limited movement of the knee during flexion and extension of the leg in a cast without restriction or physical discomfort during movement.

Another object of the present invention is to provide an improved bi-axial orthotic-cast brace assembly which permits and provides for use on an injured knee or leg and provides prevention of further injury or strain by optionally selected pre-determined locked angle positions of the cast brace.

Another object of the present invention is to provide a paired configuration of rigid bi-axial hinged side orthotic-device pivotally hinged to upper and lower flex bar and attachment anchors for easy securing, movement limit adjustment and removal optionally in cast material on the wearer's leg.

It is another object to provide such a modified bi-axial orthotic-cast brace and stabilizer that does not interfere with normal extension and flexion of the wearer's leg while in the cast, while preventing sidewise motion of the knee-joint whether the leg is flexed or extended giving added support and comfort thereto and providing rotational stability.

The orthotic device assembly of the present invention includes a bracing structure comprising a rigid support bar substantially having a center bar, said bar is optionally concave off-set and at one end pivotally hinged to an upper flange and at the other end pivotally hinged to a lower flange, thus forming the bi-axial hinge. The center bar, having the optional concave off-set of the rigid support, is placed along side the knee-joint.

In preferred embodiments, the present invention encompasses at least one improved orthotic device as a functional bracing structure for knee stabilization and derotational for support and protection of a knee-joint and leg, said device described as a double hinged, bi-axial orthotic device comprising a rigid support structure having an optional off-set or involved design through its center portion. Butt-joint hinges provide a less cumbersome hinge arrangement. Said off-set is optionally formed by raising the center bar or rod by bushings or spacers, or by bending of the center rod or bar, or by bending the upper and lower flanges and connected there between on the raised portion of each flange a flat straight support bar or rod. The upper flange to which the upper end of the rigid center support structure is pivotally hinged to the wearer's upper leg embedded in the cast material above the knee-joint for movement with the upper leg and limited motion parallel to the upper leg, and lower flange to which the lower end of the center rigid support structure is pivotally hinged to the wearer's lower leg embedded in the cast material below the knee-joint for movement with the lower leg and limited motion parallel to the lower leg. The support and stabilizing structure has a rigid center support bar or rod optionally having an off-set through its center portion and doubly hinged each at the upper and lower end of the center rigid support bar. If the off-set is accomplished by bending the upper and lower flanges, or if the bushings are used to achieve the off-set configuration, then the center rigid support bar or rod is flat and straight between the flanges. The movement of the leg by normal flexion and extension of the wearer's knee is freely permitted by the double hinged arrangement. The movement comprises any manner consistency with the bi-axial double hinged action permitted by the center rigid support bar and normal to the plane of the center rigid support bar, thereby producing functional bracing and support to the fracture site and preventing sidewise motion of the knee-joint. Preferably, a pair of indexing blocks are used.

Other objects, features and advantages will appear from the following description of a preferred embodiment of the invention, taken together with the attached drawings, in which:

FIG. 1A and 1B Detailed view—index blocks in place in the center support bar coacting with the curved end of the pivoting flex bars.

FIGS. 2, 2A, 2B—Perspective view of the curved flex bar; upper leg and lower leg curved flex bars.

FIGS. 3 and 3A—Detailed view of an index block for regulating or restricting movement in the orthotic device.

FIGS. 4, 4A and 4B—Detailed view of center bar housing for index block.

FIGS. 5A and 5B—Detailed view of alternative arrangement of index blocks positioned on flex bars and interacting with the contoured ends of the center bar.

The improved orthotic device assembly consists essentially of a bracing structure consisting essentially of a rigid center support bar or rod 1 substantially having a flat center portion; at least one indexing block 3 is removably secured 7 next to the end of the center bar in close proximity to the flex bar attachment at each end 8 of said center portion, there is pivotally hinged thereto flex bars 2. Securely attached to each flex bar 2 there are optionally attachment wings or anchor flanges 4. The attachment anchors 4 are used to assist in positioning and embedding the extensing flanges into the casting material to secure the cast brace to the casting material. Alternative to the optional attachment wings or anchor flanges, the extension flange itself may be flared to stimulate the attachment or anchor flanges. The flanges can be contoured with bending irons to allow flush apposition to the cast.

Referring to the drawings, FIGS. 1A-5B, the orthotic device of the present invention includes a single rigid support bar or rod 1 having, through the center portion, a support bar or rod 5 with a linear channel 20 with a longitudinal slot for insertion and removal of the index blocks 3. The support bar or rod 1 has two spaced end portions 21 and 22, which are continuations of the center support bar or rod. Each end portion is provided with an opening which accommodates a means for pivotally fastening at 8 to each end portion of the support bar or rod to flex bar 2. Each flex bar 2 is pivotally fastened at 8 to each end portion of the rigid support bar or rod in close proximity to cooperate with the indexing blocks 3. Such pivotal connection and coaction with the index blocks 3 of the cast brace, as discussed in the following.

Each of the flex bars 2 are terminated integrally with optional attachment anchors. Each attachment anchor 4 is provided perpendicular to the connecting flange. Alternatively, the flanges may be flared to simulate the attachment anchors. The flex bars 2 terminated by attachment anchors 4 or flaring of the flex bars are generally parallel to the upper and lower parts of the wearer's leg even at flexion or extension. The flex bars 2 and optional attachment anchor 4 which are securely fastened 9 to each other or if flared flanges, are embedded into the casting material. Thereby, the orthotic device is used in a modified cast or fracture brace and becomes an integral part of the cast, stabilizer or brace.

The center portion 1 of the orthotic device can be optionally designed off-set or involuted design to avoid pressure against the knee-joint of the wearer. Preferably a linear configuration. Various alternative configurations are possible for attachment and positioning of the center portion 5. The pivotally mounted flex bars 2 anchors 4 or flared flanges are securely embedded in the cast material on the wearer's leg, flex bar and attachment anchors, or flared flanges, in the upper part of the cast above the knee-joint and flex bar and attachment wing, flared flanges, in the lower part of the cast below the knee-joint. The three part construction with the double hinged action allows the stabilizer to translate the normal leg action of extension and flexion into the conformed and supported orthotic bracing structure integral with the cast. The combination of motions permitted by the three part construction results in the motion of the attachment wings and flanges with respect to the rigid support bar or rod that closely parallels that natural action of the knee-joint. The rigid support bar or rod 1 closely and accurately follows the action of the wearer's knee and at all times continuing to provide support and stability to the knee joint while the leg is in a cast. Especially protection against sidewise forces and rotational stability is provided.

The improved orthotic device used in a modified cast brace is attachable to the inner or outer leg. Preferable the orthotic device in a modified cast brace is positioned and secured in paired configuration on both sides of the knee opposite the orthotic center of the knee to provide rotational stability. The center portion of the rigid support bar or rod is placed directly over the medial or lateral ligament.

By the double hinge bi-axial arrangement, the motions of flexion or extension are easily followed by the modified cast brace employing the orthotic device with the accompanying cast support. The principle upon which the invention is based, as well as the operation of the three-segment hinged arrangement, is best understood by referring to FIG. 1A–FIG. 5B. The bracing structure remains generally parallel to the knee-joint, but the action of the joint formed by the stabilizer accurately parallels the action of the individual wearer's knee. At all times, the orthotic device and knee stabilizer of the modified cast brace of this invention remains substantially displaced, but parallel and adjacent to the knee-joint, continuing to provide protection and support. Translational motion of the stabilizer of the modified cast brace is limited by being secured into the casting material.

By using the present invention, it is thus possible to have a convenient, effective and comfortable means for stabilizing and supporting the leg and knee-joint and thereby eliminate discomfort or possible injury or reinjury to the leg. More importantly, the improved bi-axial orthotic device prevents change in position which otherwise is attributed to rotating forces on the fracture site. The double hinge arrangement is a novel feature among orthotic devices as used in modified cast braces and fracture braces. Also, the center portion of the rigid support bar or rod of the knee stabilizer of the cast brace is novel in that it does not place pressure on the knee-joint. Acting together, the improved bar or rod and double hinge bi-axial arrangement with means for limiting and and restricting movement of the leg by means of the index blocks from the basis for an original and useful improvement in the design, function and operation of the present orthotic device.

Although a direct comparison between the present construction and other presently known conventional cast brace structures is difficult, it is the opinion of persons who have used the orthotic device in a modified cast brace that more than satisfactory results were obtained. For example, football players, who had each experienced leg injuries, wore the described orthotic device stabilizer and cast brace. By being able to have some motion to the injured leg, rehabilitation and full use of the leg was enhanced. Each player was then able to perform his prescribed duties without extended recuperation. Joint motion and muscle function are maintained so that they are at a functional level at the completion of the treatment.

In use, the orthotic device used in an improved modified cast brace is used in a cast brace assembly which protects healing structures from disruptive stresses on the leg or knee especially rotational forces. In the use, the modified cast brace assembly with the orthotic device is employed in a leg cast on patients with a variety of problems in fractures of the proximal tibia and distal femur. Among the knee and leg problems, including acute ligamentous injuries, medial and lateral reconstructions, cruciate ligament prosthesis, total knee arthroplasties, tibial plateau fractures, and patello-femoral arthro-plasties.

In conjunction with the bi-axial hinge arrangement the novel feature of the present invention includes index blocks 3, preferably used in paired configuration the index block is positioned transversely on a plane with the longitudinal flex bars. The index blocks 3 are preferably positioned on said center bar 1 to cooperate with the pivoting attaching end 10 of the flex bar. Engraved or stamped on each index block are indicia of position. In the center bar cover plate 18 there are sight openings 16 for viewing the index block 3 setting to the predetermined angle and limit of motion of the flex bars.

Each index block 3 has a plurality of sides. Each side has a shaped face 12 forming the contoured peripheral configuration of the index block to interact with the curved end of the flex bar at 10 and flat face surface 14 to firmly restrict and lock the index block 3 against the back of the center bar 23. The curved or shaped face of each index block 12 is cam-like contoured for cooperation with the rounded pivot end of the flex bars 2 each side of the index block has a complimentary configuration of angles and stops which coact with the pivoting end of the flex bar as the flex bar pivots. Hence the index block is juxtapositioned to interact with the curved end of the flex bar.

The improved orthotic device described herein with the indexing means 3 for restricting the range of motion, the bi-axial hinge and consequently of the leg, generally from the locked position at 0 degrees to about 60 degrees, the arc and total range of motion may be varied according to the individual pathology. Further, by adjustments made by changing the settings in the indexing blocks 3, predetermined flexion limits, for example, from about 20 to about 110 degrees. Also, extension limits can be set by means of the indexing blocks from 0 to about 60 degrees. Flexion limit at 110 degrees is useful for rehabilitation. The improved bi-axial cast brace with indexing blocks permits isotonic, isometric and progressive resistance exercises while in the cast brace. The cast is worn from six to eight weeks or for a time period as required.

The hinged long leg cast including the bi-axial hinged three-segment-brace support with index blocks 3 is practical from the standpoint of cost, time and ease of application. Also, the comfort to the patient is notable, both in ease of movement or limited predetermined movement when permitted, in weight and functional stability and support. Another distinct advantage of the modified cast brace is the possible reuse of the bi-axial joint which lessens the cost.

More particularly, a notable advantage to the use of the instant orthotic device as a modified cast brace assembly with the three-segment bi-axial hinged brace is the ease of application. Many other cast brace joints and assemblies require the joints need to be aligned parallel and over the axis of rotation of the knee. This critical alignment requires an alignment jig—a special tool is required. The instant joint is unique since it does not require special alignment. It is sufficient to place one joint on each side of the knee with the placement reasonably determined over the center of rotation for the knee. Orientation of the joints and extensions contoured to the upper and lower leg curvature allows ease of placement in the case with maximum comfort to the patient.

When applying the orthotic device in a modified cast brace with the joint in place, plaster may be used as a general cast material. Some of the newer synthetic materials may be more durable with active athletic patients. Also, newer synthetic materials are lighter in weight than plaster. In use of any casting material, the joints are then easily applied to the cast by implanting the extended flanges and attachment wings thereto. Means for integral attachment of the orthotic device to the casting material is provided.

Within the embodiment of this invention is the means for regulating and restricting the movement of the cast brace by means of the index blocks 3. Because of the each of movement of the knee fitted with an improved cast brace, including the orthotic device, there is a need for a means for regulating and restricting the movement of the leg accomplished by the index blocks 3. Confined movement is often recommended at early stages of healing. Later, freer movement of the knee and leg can be permitted. The index blocks provide an easy means for changing the movement to predetermined limits. Therefore, patients with operated cases fail to require longer time for recovery of motion. Repaired knees which "loosen" during immobilization does not apply to cases employing the instant device. Therefore, legs treated with early protected motion show no harm and enhance recovery and early full use of the knee joint.

Also included within the invention, is the means for angular positioning of the leg. Also, included is a stop and index means for limiting the folding movement and angle of the mechanical double hinged joint. There is capability for free movement of the knee, restricted movement and fixed angular positioning of the knee-joint. Varied capability to control the knee and leg movement gives early protected motion, with early limited knee motion, followed by free motion. Actually, motion can be initiated at any time, if the patient has a condition which will permit movement. Restriction of movement can be accomplished easily by means of the indexing blocks 3 as described herein.

The feature of the orthotic device in the modified cast brace is the three-segment double hinged joint with index blocks 3 uncommon to other fracture braces. In addition, the modified cast brace is provided with limited movement and stop means for adjusting to limit both flexion and extension of the leg and knee-joint, pre-set and resettable means for added freedom in setting a range of knee motions utilizing the novel index blocks. Setting can range from a locked position to a limited motion to a completely adjustable brace to desired limits.

The modified cast brace can be applied with conventional casting materials. For example, if a long leg cast is suitable to the pathology, it can be applied as over a cast sock and elastic knee cage. These items are optional. Additionally, felt pads may be placed over the malleoli, the extensor hallucis longus tendon on the dorsum of the foot, and the peroneal nerve. An additional piece of felt may be placed over the patella to create an identifiable bump for trimming and to turn the edges away from the shin. The modified cast brace with the improved orthotic device in paired configuration is embedded in the casting material on each site of the knee-joint.

The present invention relates to a three segment bi-axial hinged orthotic device without geared or other direct interacting connection of the flex bars are flange arms. This results in independent motion of each hinged flex bar with respect to the center bar. Each bi-axial pivot point eliminates the lever-effect on a geared or otherwise directly connected or interacting device having a single or substantially single hinged pivot point. Also in the present orthotic device the bi-axial hinge arrangement results in a delocalized fulcrum point so that the load is spread out from a single point to the flex bars or flange arms.

The modified cast brace with the improved orthotic device of this invention is useful in many ailments of the leg, knee and knee ligaments. Both pre- and post-operative utility has been realized. Chronic and acute knee and knee ligament injuries can be treated and rehabilitated. In most cases, rehabilitation time after treatment was shortened. Quadriceps and hamstring tone rated fair to good on removal of the modified cast brace. Loosening of repaired knees can be prevented since complete immobilization is not required.

While certain novel features of the invention have been disclosed herein, and pointed out in the annexed claims, it will be understood that, in accordance with the doctrine of equivalents, various omissions, substitutions and changes may be made by those skilled in the art without departing from the spirit and scope of the invention.

What is claimed is:

1. A bi-axial orthotic device having
   (1) a center bar having pivot points for attachment of independent flex bars one near each end and a pair of independent indexing blocks removably positioned therebetween;
   (2) said flex bars pivotally attached through pivoting ends on each flex bar to each end of the center bar and extending longitudinally therefrom terminating in transverse anchor plates, the attached pivoting end of the flex bars contoured to cooperate with the indexing blocks each in close proximity and positioned to coact with said indexing blocks;
   (3) independent index blocks securely but removably attached and positioned on said center bar to cooperate with said attaching end of said flex bars each index block having a plurality of sides each side a cam contoured for cooperation with said pivoting end of said flex bar to regulate the movement and angle of said flex bar.

2. A bi-axial orthotic device as defined in claim 1 further including (1) index blocks having a plurality of sides, each side contoured to produce a predetermined movement and angle of the flex bars and a stop, said sides coacting with the pivoting end of the flex bar the pivot end of the flex bar having a stop notch, said flex bar follows the contoured sides to the stop;

(2) each index block removeably mounted on the center bar interacts independently with the axially mounted flex bar.

3. In a bi-axial orthotic device as defined in claim 1 having a longitudinal center bar, a pair of flex bars each pivotally attached to each end of the center bar, said center bar having at least one index block formed by a plurality of contoured sides with stops, said index blocks removably attached on the center bar positioned to coact with the pivoting attached end of a flex bar having a complementary interacting stop notch.

4. A bi-axial orthotic device as defined in claim 1 wherein said center bar consisting of a housing to accept an index block, means for securely removably fastening the index block in said housing, said center bar having a pivotal fastening point for longitudinal flex bars, flex bars having complementary pivotal attached end and positioned for engagement with the index blocks to provide preselected angle between the flex bars.

5. In a bi-axial orthotic device as defined in claim 1 having index blocks each block having a plurality of sides each side having a specific complementary configuration of angles and stops which coact with the pivoting end of the flex bar as the flex bar pivots and the complementary pivoting end of the flex bar so positioned to coact with the adjacent side of the index block following the contoured peripheral configuration of the index block.

* * * * *